US010076473B2

(12) United States Patent
Park

(10) Patent No.: US 10,076,473 B2
(45) Date of Patent: Sep. 18, 2018

(54) APPARATUS AND METHOD FOR MANUFACTURING DRIED GEL SHEET AND GEL SHEET OR BEAUTY PACK MANUFACTURED BY THE SAME

(71) Applicant: C&TECH CORPORATION, Hwaseong-si (KR)

(72) Inventor: Han-Wook Park, Seoul (KR)

(73) Assignee: C&TECH CORPORATION, Hwaseong-si (KR)

( * ) Notice: Subject to any disclaimer, the term of this patent is extended or adjusted under 35 U.S.C. 154(b) by 57 days.

(21) Appl. No.: 15/242,671

(22) Filed: Aug. 22, 2016

(65) Prior Publication Data

US 2017/0231876 A1      Aug. 17, 2017

(30) Foreign Application Priority Data

Feb. 15, 2016   (KR) .................. 10-2016-0017223
May 17, 2016   (KR) .................. 10-2016-0060415
(Continued)

(51) Int. Cl.
*A61K 8/02*      (2006.01)
*A61K 8/04*      (2006.01)
(Continued)

(52) U.S. Cl.
CPC ............ *A61K 8/042* (2013.01); *A61K 8/0212* (2013.01); *A61Q 19/00* (2013.01); *B05D 1/18* (2013.01); *B05D 3/007* (2013.01); *B29D 7/01* (2013.01)

(58) Field of Classification Search
USPC ............ 156/247, 248, 250, 267, 269, 306.6, 156/306.9, 307.1, 307.3, 307.5, 307.7,
(Continued)

(56) References Cited

U.S. PATENT DOCUMENTS 3,885,078 A * 5/1975 Wichterle ................ A61K 9/70
427/243
4,220,153 A * 9/1980 Dresback ............. A61K 9/0068
424/438
(Continued)

FOREIGN PATENT DOCUMENTS

KR   1019960703019      6/1996
KR      20-0381099      4/2005
(Continued)

*Primary Examiner* — Sing P Chan
(74) *Attorney, Agent, or Firm* — Lex IP Meister, PLLC

(57) ABSTRACT

The present invention provides a dried gel sheet manufacturing apparatus and method, and a gel sheet. The dried gel sheet manufacturing apparatus includes an applying unit 2 which includes gravure rolls 22*a* and 22*b* to apply a hydrogel composition of a reserving tank 24 on a supporting member M which is conveyed together with a lower film Fa to form a sheet shaped hydrogel H, a cooling drying unit 4 which cools the sheet shaped hydrogel H using a cooling plate 44 to be solidified while being transported; and a heating drying unit 6 which dries and irons the solidified sheet shaped hydrogel by a combination of a heater roll group 64 and a nozzle unit 66 or the nozzle unit 66, a dry conveyer 68, a godet roller 70 or a nozzle unit 66, a dry conveyer 68, a heater roll group 64, or a nozzle unit 66 and a godet roller 70 to obtain a gel sheet G2. Further, a dried gel sheet manufacturing method through the apparatus includes an applying step of forming a sheet shaped hydrogel H by a lower film Fa and protecting the sheet shaped hydrogel by adhering the upper film Fb on a top surface; a cooling drying step of passing the sheet shaped hydrogel H at a low temperature atmosphere to be solidified, and a heating drying step of receiving and separating the upper and lower films Fb and Fa from the sheet shaped hydrogel H which is solidified by the cooling and heating and drying the front and rear surfaces by ironing the sheet shaped hydrogel to collect (Continued)

the gel sheet S2. Through the manufacturing method, a gel sheet G2 which is formed to be a film so that density of the front and rear surfaces is higher than a center portion and a beauty pack obtained by pressing the gel sheet S2 by the mask member MP are suggested.

2 Claims, 20 Drawing Sheets

(30) Foreign Application Priority Data

May 25, 2016 (KR) .......................... 10-2016-0064215
Jun. 13, 2016 (KR) .......................... 10-2016-0073417

(51) Int. Cl.
*A61Q 19/00* (2006.01)
*B05D 1/18* (2006.01)
*B05D 3/00* (2006.01)
*B29D 7/01* (2006.01)

(58) Field of Classification Search
USPC ...................................... 156/701, 714, 719
See application file for complete search history.

(56) References Cited

U.S. PATENT DOCUMENTS

| 5,300,192 | A | * | 4/1994 | Hansen | A61F 13/0209 156/296 |
| 5,354,823 | A | * | 10/1994 | Tseng | C08F 226/06 525/326.9 |
| 5,393,798 | A | * | 2/1995 | Weber | A61L 15/24 424/78.02 |
| 5,393,825 | A | * | 2/1995 | Tseng | C08F 226/06 524/548 |
| 5,423,736 | A | * | 6/1995 | Cartmell | A61B 17/085 602/42 |
| 5,429,589 | A | * | 7/1995 | Cartmell | A61B 17/085 424/443 |
| 5,478,308 | A | * | 12/1995 | Cartmell | A61B 17/085 602/42 |
| 5,609,727 | A | * | 3/1997 | Hansen | A61F 13/0209 162/158 |
| 6,096,333 | A | * | 8/2000 | Rolf | A61K 9/7061 424/443 |
| 6,455,065 | B1 | * | 9/2002 | Hymes | A61K 8/0208 424/400 |
| 6,495,158 | B1 | * | 12/2002 | Buseman | A61K 8/0208 424/401 |
| RE38,185 | E | * | 7/2003 | Joulia | A45D 33/00 264/316 |
| 6,855,743 | B1 | * | 2/2005 | Gvozdic | C08J 3/075 264/41 |
| 7,419,677 | B2 | * | 9/2008 | Gueret | A45D 40/26 424/400 |
| 8,142,592 | B2 | * | 3/2012 | Miller, II | B32B 37/02 156/230 |
| 8,524,272 | B2 | * | 9/2013 | Miller, II | A61M 35/00 424/443 |
| 8,802,136 | B2 | * | 8/2014 | Miller, II | A61M 35/00 424/443 |
| 9,358,373 | B2 | * | 6/2016 | Miller, II | A61M 35/00 |
| 9,731,490 | B2 | * | 8/2017 | Miller | B32B 38/04 |
| 2003/0072792 | A1 | * | 4/2003 | Flanigan | A61K 9/703 424/449 |
| 2003/0124162 | A1 | * | 7/2003 | Ueda | A61K 8/0208 424/401 |
| 2010/0239621 | A1 | * | 9/2010 | Tsujihata | A61K 8/0208 424/401 |
| 2013/0287958 | A1 | * | 10/2013 | Oouchi | B01D 67/0011 427/374.1 |
| 2017/0050364 | A1 | * | 2/2017 | Korley | B29C 47/0004 |

FOREIGN PATENT DOCUMENTS

| KR | 10-2007-0099083 | 10/2007 |
| KR | 10-1134096 | 4/2012 |
| KR | 10-1366682 | 2/2014 |
| KR | 10-1372227 | 3/2014 |
| KR | 10-1522006 | 5/2015 |
| KR | 10-1597794 | 2/2016 |

* cited by examiner

APPARATUS AND METHOD FOR MANUFACTURING DRIED GEL SHEET AND GEL SHEET OR BEAUTY PACK MANUFACTURED BY THE SAME

CROSS-REFERENCE TO RELATED APPLICATION

This application claims priority to and the benefit of Korean Patent Application No. 10-2016-0017223, 10-2016-0060415, 10-2016-0064215, and 10-2016-0073417 filed in the Korean Intellectual Property Office on Feb. 15, 2016, May 17, 2016, May 25, 2016, and Jun. 13, 2016, the entire contents of which are incorporated herein by reference.

BACKGROUND OF THE INVENTION

(a) Field of the Invention

The present invention relates to an apparatus and a method or manufacturing a dried gel sheet which implements mass production of a product formed of a hydrogel material and a gel sheet or a beauty pack manufactured by the same.

(b) Description of the Related Art

Polymer hydrogel is frequently used for disposable diapers, contact lenses, metical electrodes, or cell culture. For a specific purpose, the polymer hydrogel is also used for various fields such as a plastic surgery material or soil moisture storage, or a bandage for burn wound.

The hydrogel is a hydrophilic polymer which is cross-linked by cohesive force by a covalent bond, a hydrogen bond, a Van der Waals bond, or a physical bond. The hydrogel has a three-dimensional network structure which contains a large amount of water therein to swell. Therefore, when the hydrogel absorbs water, the hydrogel shows a behavior similar to biological tissue.

When a product is formed of hydrogel, the product is very strong even at a temperature of 90° C. Further, even though the product is modified due to external force, molecules quickly rearrange themselves to recover its original structure.

Generally, the hydrogel uses aqueous solution obtained by melting polyhydric alcohol such as glycerin or butylene glycol, Ceratonia silique gum, agar, carrageenan, or xanthan gum in water maintained at 90 to 100° C. as a main component and is obtained by mixing and distributing an additive in the aqueous solution to be thickened to be a gel type.

However, the hydrogel contains a large amount of moisture so that the hydrogel has a weak property of matter. Therefore, there are lots of difficulties to manufacture a product by applying the hydrogel.

For example, during the process of manufacturing a hydrogel mask pack, the manufactured hydrogel is provided between two films having good elasticity and is stretched to have a sheet shape and then cooled. Thereafter, the hydrogel is pressed together with the film during the press process to have a mask shape.

According to the above-described manufacturing method, the hydrogel which is pressed to have a mask shape has a weak property of matter so that the hydrogel needs to be protected as a film and the manufactured hydrogel mask needs to be sealed in order to be stored. Therefore, the manufacturing process thereof is complicated.

In order to solve the above-mentioned drawback, Patent Document 1 discloses a method of forming a curing film on a surface of a hydrogel. However, even though the curing film is applied to the hydrogel, the original weak property of material is never changed. Therefore, Patent Document 1 does not suggest a fundamental solution.

In the meantime, when the hydrogel which is stretched to have a sheet shape is naturally dried, the hydrogel is changed to a gel sheet. Therefore, it is easy to cut out the hydrogel to have an arbitrary shape. Further, it is convenience because when water is supplied to the cut-out gel sheet, the hydrogel swells again to be used as an original hydrogel.

However, a large space which is separated from the outside and a large amount of time and effort are required to naturally dry the hydrogel, which is not suitable for mass production.

Patent Document 2 discloses an example which manufactures a therapeutic medical device formed of dried hydrogel from hydrophilic hygroscopic polymer such as an unmodified or modified polymeric carbohydrate in the form of a solid foam which is prepared by freeze-drying a hydrogel.

However, it is difficult to freeze-dry the hydrogel and the frozen moisture is melted at a room temperature to be absorbed again as a hydrogel. Therefore, it is inconvenient because the hydrogel needs to be stored in a frozen state before using the hydrogel.

Patent Document 3 discloses an example in which a hyaluronic gel sheet which is obtained by primarily drying the hydrogel obtained by applying aqueous solution in which an alkali salt of polymer hyaluronic acid is melted in an alkali solution to produce an even sheet shape in a vacuum oven is dipped an anhydride solution diluted by an undiluted solution with low molecular weight organic acid or an unit organic acid which forms the anhydride and then took out from the anhydride solution to secondarily dry in a vacuum oven.

However, it is difficult to dry a large amount of hydrogel in the vacuum oven. Therefore, the method suggested in Patent Document 3 is not suitable for mass production.

The above information disclosed in this Background section is only for enhancement of understanding of the background of the invention and therefore it may contain information that does not form the prior art that is already known in this country to a person of ordinary skill in the art.

RELATED ART DOCUMENT

Patent Document

Korea Registered Patent No. 10-1372227
Korea Patent Laid-Open Publication No. 10-1995-0705867
Korea Registered Patent No. 10-1597794

SUMMARY OF THE INVENTION

The present invention has been made in an effort to provide a dried gel sheet manufacturing apparatus which is capable of continuously drying a hydrogel which is manufactured to have a continuous sheet shape.

The present invention has been made in an effort to further provide a manufacturing method using a dried gel sheet manufacturing apparatus which quickly dries the hydrogel by heating the hydrogel while ironing the hydrogel to trim front and rear surfaces of the hydrogel which is manufactured to have a continuous sheet shape.

The present invention has been made in an effort to provide a gel sheet which is manufactured by the above-described manufacturing method so that a density of the front and rear surfaces is higher than that of a center portion.

The present invention has been made in an effort to further provide a beauty pack based on the gel sheet manufactured by the above-described manufacturing method.

An exemplary embodiment of the present invention provides a dried gel sheet manufacturing apparatus, including an applying unit which covers an upper film with a top surface while conveying a sheet shaped hydrogel obtained by applying a hydrogel composition reserved in a reserving tank on a supporting member which is conveyed together with a lower film by gravure rolls to have a constant thickness; a cooling drying unit which conveys the sheet shaped hydrogel protected by upper and lower films by a conveyer to a lower side of a cooling plate to be cooled to be converted into a sheet shaped solidified gel; and a heating drying unit which passes a sheet shaped solidified gel in which the upper and lower films are separated through a heater roll group formed by a plurality of hearer rolls including a nozzle unit which supplies warm air in a heating housing to iron and heat and dry the front and rear surfaces of the sheet shaped solidified gel with a warm air to be converted into a gel sheet.

Another exemplary embodiment of the present invention provides a dried gel sheet manufacturing apparatus of the exemplary embodiment of the present invention including an applying unit which covers an upper film with a top surface while conveying a sheet shaped hydrogel obtained by applying a hydrogel composition reserved in a reserving tank on a supporting member which is conveyed together with a lower film by gravure rolls to have a constant thickness; a cooling drying unit which conveys the sheet shaped hydrogel protected by upper and lower films by a conveyer to a lower side of a cooling plate to be cooled to be converted into a sheet shaped solidified gel; and a heating drying unit which passes a sheet shaped solidified gel in which the upper and lower films are separated through a heater roll group formed by a plurality of heater rolls including a nozzle unit which supplies warm air in a heating housing to iron and heat and dry the front and rear surfaces of the sheet shaped solidified gel with a warm air to be converted into a gel sheet.

Further, Yet another exemplary embodiment of the present invention provides a dried gel sheet manufacturing method including: an applying step of applying a hydrogel composition on a supporting member which is supplied along the lower film and adhering an upper film thereon to protect a sheet shaped hydrogel; a cooling drying step of converting the sheet shaped hydrogel into a sheet shaped solidified gel under a low temperature atmosphere, and a heating drying step of separating upper and lower films from the cooled sheet shaped solidified gel and ironing front and rear surfaces to collect a dried gel sheet.

In the heating drying step of the dried gel sheet manufacturing method, a releasing paper may be added on a top surface of the sheet shaped solidified gel obtained by separating the upper and lower films.

In a gel sheet according to an exemplary embodiment of the present invention obtained by the above-described manufacturing method, a front surface or a rear surface is ironed so that the gel sheet is formed to be a film in which a density of the front or rear surface is higher than a center portion.

Further, in a beauty pack which is formed of a dried gel sheet according to an exemplary embodiment of the present invention, front and rear surfaces or one of the front and rear surfaces of the sheet-shaped solidified gel may be ironed so that the gel sheet is formed to be a film in which a density of the front or rear surface is higher than a center portion.

Further, in a beauty pack which is formed of a dried gel sheet according to an exemplary embodiment of the present invention, the surface of the sheet shaped solidified gel may be ironed by the above-described manufacturing method to be a film. Further, a wet strength paper may be added to an opposite rear surface.

In the beauty pack which is formed by a dried gel sheet of the present invention, a cosmetic component powder or aqueous solution may be provided between a surface which is formed to be a film and the wet strength paper added thereon.

According to the dried gel sheet manufacturing apparatus of the above-described exemplary embodiment of the present invention, a gravure roll continuously applies a hydrogel composition on front and rear surfaces of a supporting member and a cold plate cools down the sheet shaped hydrogel which is being transported at a low temperature to convert the hydrogel into a sheet shaped solidified gel. Further, a heating roller group receives the sheet shaped solidified gel such that upper and lower films are separated from each other and the sheet shaped solidified gel is completely dried by being ironed and dried with warm air. Therefore, the hydrogel based gel sheet is continuously manufactured, which is suitable for mass production.

According to the dried gel sheet manufacturing method using a dried gel sheet manufacturing apparatus of the above-described exemplary embodiment of the present invention, hydrogel applied between upper and lower films is cooled at a low temperature to be converted into a sheet shaped solidified gel. Thereafter, the upper and lower films are separated and then front and rear surfaces those of are ironed and heated and dried with warm air. Therefore, a density of front or rear surface is higher than that of a center portion in which the supporting member is buried so that the gel sheet which is formed to be a film may be continuously provided.

According to the gel sheet obtained by the dried gel sheet manufacturing apparatus of the exemplary embodiment of the present invention, even though the gel sheet swells to be an original hydrogel by dipping the gel sheet in a drug or cosmetic component, a density of a part of the front and rear surfaces which is formed to be a film is maintained to be higher than that of the center portion. Therefore, when the gel sheet is adhered on a skin to be used, vaporization of the drug or the cosmetic component of the hydrogel through the surface of the hydrogel is suppressed. As a result, the drug or cosmetic component is in contact with the tissue through a sufficient time.

Further, the beauty pack of the exemplary embodiment of the present invention which is obtained by the above-described manufacturing method is maintained to be a gel sheet before swelling. Therefore, even though the gel sheet is folded to be four parts, the gel is not broken at a folded portion. Therefore, there is no need to add an elastic resin film like the related art. Accordingly, even though the used beauty pack may be discarded as it is, the gel which is decomposed by microorganism is discarded, which does not influence environment contamination.

In the beauty pack formed of a dried gel sheet of the exemplary embodiment of the present invention, the added wet strength paper also serves as a release paper. Therefore, even though the beauty pack is packed in a folded state, when the beauty pack is used, the beauty pack may be simply unfolded using the wet strength paper so that it is easy to treat the beauty. In the beauty pack formed of a dried gel sheet of the exemplary embodiment of the present invention, when the cosmetic component is packed in the pouch, the cosmetic component provided between the wet strength paper and the surface which is formed to be a film is protected by the wet strength paper so that the cosmetic component is not dissipated. When a user uses the pack on a face, a high concentration cosmetic composition provided on a surface from which the wet strength paper is removed is directly supplied onto the skin, so that effect of beauty care is doubled.

Particularly, even though the added amount of an essential cosmetic composition which is expensive is limited to minimum, the essential cosmetic composition is entirely supplied to the user without wasting the essential cosmetic composition. Therefore, cost is reduced by providing a minimum amount of the expensive cosmetic composition but the effect of beauty care may be fully provided.

DETAILED DESCRIPTION OF THE EMBODIMENTS

Hereinafter, a dried gel sheet manufacturing apparatus and method, and a gel sheet manufactured by the same of the present invention will be described in detail with reference to the attached drawings.

Figure 1:
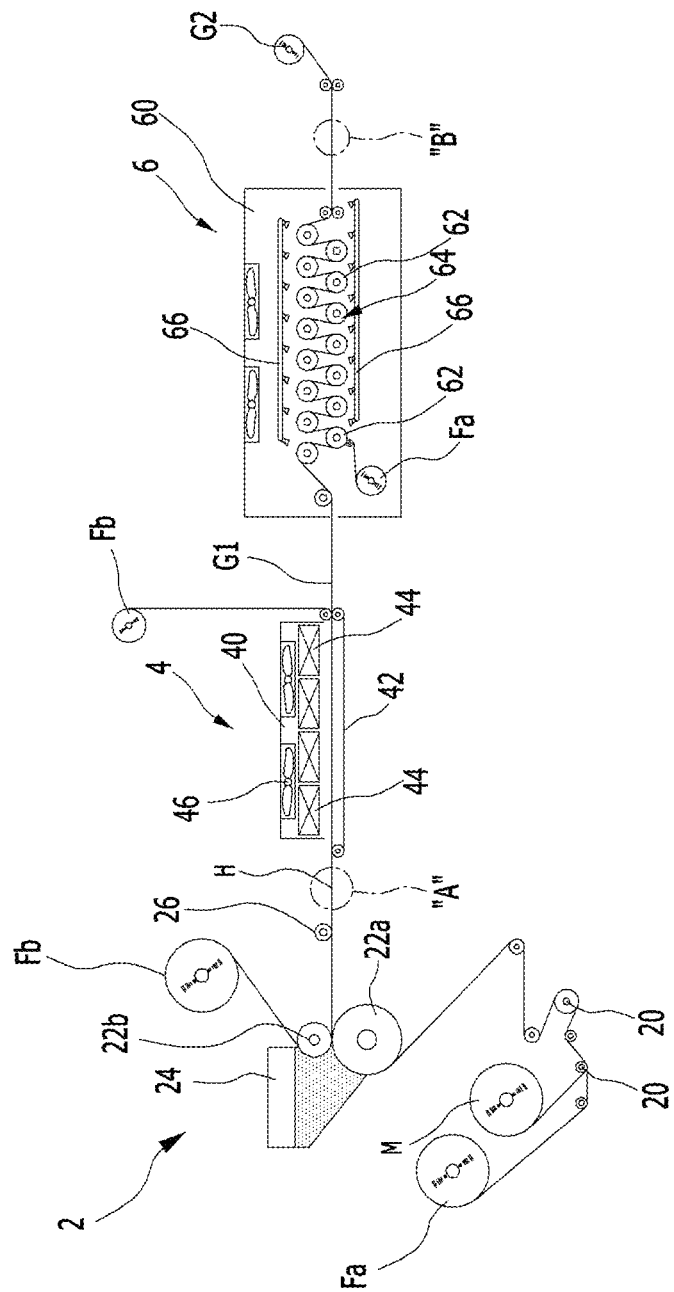
FIG. 1 is a schematic diagram of a dried gel sheet manufacturing apparatus according to an exemplary embodiment of the present invention.

FIG. 1 illustrates a dried gel sheet manufacturing apparatus of the present invention, which includes an applying unit 2, a cooling drying unit 4, and a heating drying unit 6.

The applying unit 2 is configured by a plurality of guiding rolls 20, gravure rolls 22a and 22b, and a reserving tank 24 in which a hydrogel aqueous solution H is reserved.

The cooling drying unit 4 is partitioned by a cooling housing 40 provided with an inlet and an outlet at both sides and a conveyer 42 is disposed on a lower surface in the cooling housing 40 and equipment required for low temperature cooling such as a cooling plate 44 and a ventilator 46 is disposed thereon.

The heating drying unit 6 is partitioned by a heating housing 60 provided with an inlet and an output at both sides and a heater roll group 64 in which a plurality of heater rolls 62 is continuously arranged is provided therein.

A nozzle unit 66 which supplies hot air is disposed between heater rolls 62 of the heater roll group 64 to accelerate the drying of the hydrogel.

Each heater roll 62 of the heater roll group 64 is desirably maintained at 70 to 80° C. and the hot air sprayed through the nozzle unit 66 is desirably maintained in the range of 180 to 200° C.

According to the manufacturing apparatus, in the plurality of guiding rolls 20 of the applying unit 2, overlapping a supporting member M which is formed of a lower film Fa and any one of a mesh, a thin non-woven fabric, and a thin cellulose is guided and continuously supplied to pass between gravure rolls 22a and 22b.

Figure 2:
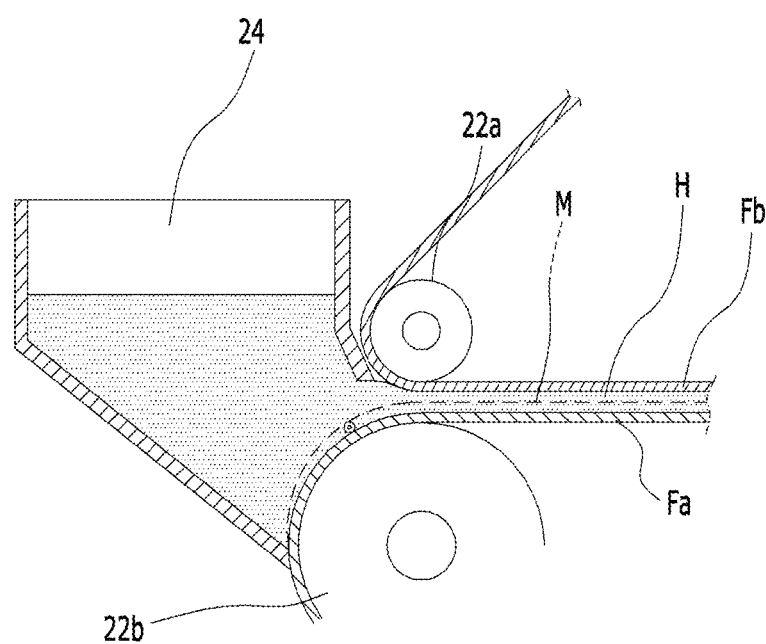
FIG. 2 is an enlarged view illustrating a state in which a hydrogel is applied by a gravure roll illustrated in FIG. 1.

The reserving tank 24 in which an aqueous state hydrogel composition is reserved is heated at 75 to 100° C. to maintain liquidity of the hydrogel composition all the time. Therefore, as illustrated in FIG. 2, the hydrogel composition passes between the gravure rolls 22a and 22b by being in contact with the surfaces of both gravure rolls 22a and 22b to adjust the thickness and is applied on the lower film Fa to form a sheet shaped hydrogel H. The sheet shaped hydrogel H formed as described above is transported along the lower film Fa with the supporting member M therein.

In the exemplary embodiment of the present invention, the hydrogel composition is provided by a mixture obtained by diluting two or more selected from natural polymers consisting of devil's tongue jelly, carrageenan, gellan gum, carob bean gum, gelatin, agar, collagen, hyaluronic acid, acacia gum, Arabic gum, starch, flurane, galactomannan, guar gum, pluronic, algin, xanthan gum, pectin, and cellulose in a distilled water.

As described above, a top surface of the sheet shaped hydrogel H which is transported along the lower film Fa is covered by an upper film Fb which is supplied through an upper gravure roll 22b and is stationed and moved along a guider 26.

The upper film Fb only serves to spread the sheet shaped hydrogel H to have a uniform thickness so that the upper film Fb is not necessarily provided and may be omitted. The guider 26 may also be omitted.

Figure 3:
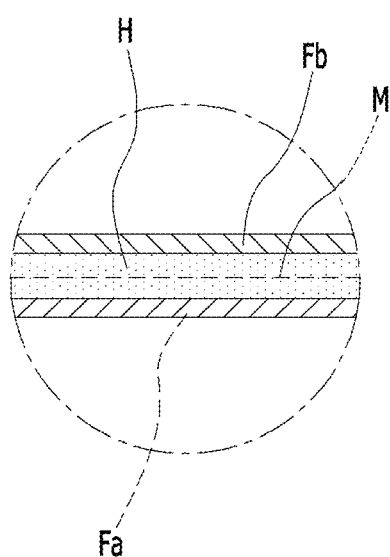
FIG. 3 is an enlarged cross-sectional view of a part "A" of FIG. 1.

As illustrated in FIG. 3, the sheet shaped hydrogel H has a single layer structure which is protected by the upper and lower films 22b and 22a to pass through the cooling drying unit 4.

Figure 4:
FIG. 4 is a photo of an actual part "A" of FIG. 1.

Further, the sheet shaped hydrogel H is formed such that moisture of the upper surface (below the upper film Fb) is checked by naked eyes before entering the cooling drying unit 4, as illustrated in the photo of the actual object of FIG. 4.

Inside of the cooling housing 40 of the cooling drying unit 4 is maintained in the range of −20 to −5° C. range so that the passing sheet shaped hydrogel H is rapidly cooled and the liquidity is lost to be changed to a sheet shaped solidified gel G1.

When the sheet shaped solidified gel G1 is discharged from the cooling housing 40, the upper film Fb which covers the upper surface there is separated and removed and the sheet shaped solidified gel continuously enters the heating housing 60 of the heating drying unit 6 together with the lower film Fa.

The lower film Fa needs to be separated at the entrance of the heating housing 60. In this case, in order to prevent the surface damage of the sheet shaped solidified gel G1 during the separating process, it is most effective to separate the lower film when the sheet shaped solidified gel passes through a first heater roll 62 at the lower side of the heater roll group 64.

The sheet shaped solidified gel G1 from which the lower film Fa is separated and removed continuously passes between the heater rolls 62 of the heater roll group 64.

In this process, the plurality of heater rolls 62 which configures the heater roll group 64 is alternately disposed to each other so that the sheet shaped solidified gel G1 passing therethrough is transported between one pair of heater rolls 62. Therefore, high speed driving is allowed while maintaining a predetermined tension.

Further, the heater rolls 62 which are alternately disposed may set a long drying course of the sheet shaped solidified gel G1 but an actual length is shortened. Therefore, there is an additional effect that an occupying space of the equipment may be reduced.

In the meantime, the arrangement pattern of the heater rolls 62 significantly affects a resistance which may be applied to the sheet shaped solidified gel G1. Therefore, it is desirable to reduce the resistance as much as possible so as to prevent the sheet shaped solidified gel from being broken or partially damaged. However, when the contact area with the heater roll 62 is reduced, the ironing effect of the sheet shaped solidified gel G1 is lowered, so that both need to be balanced.

In the exemplary embodiment of the present invention, heater rolls 62 of the heater roll group 64 which are disposed in two rows are disposed approximately in a delta shape, so that the sheet shaped solidified gel G1 which is being driven is in sufficient contact with each heater roll 62 and is applied with a reduced resistance.

As described above, when the sheet shaped solidified gel G1 passes through the heater roll group 64, a front surface and a rear surface are alternately in contact with the heater roll 62 and heated and dried. Further, the sheet shaped solidified gel G1 is ironed while the surface is pulled due to the resistance during the driving.

Further, the warm air is sprayed through the nozzle unit 66 while the sheet shaped solidified gel G1 is ironed so that the drying is accelerated and the sheet shaped solidified gel G1 is completely dried to be a gel sheet G2 and is discharged from the heating housing 60.

Figure 5:
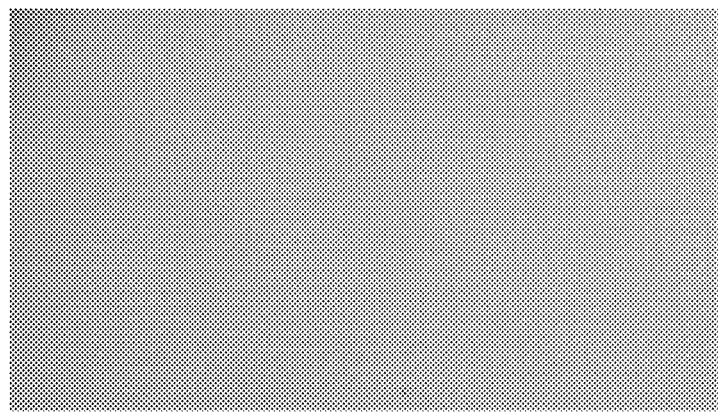
FIG. 5 is a photo of an actual part "B" of FIG. 1.
Figure 6:
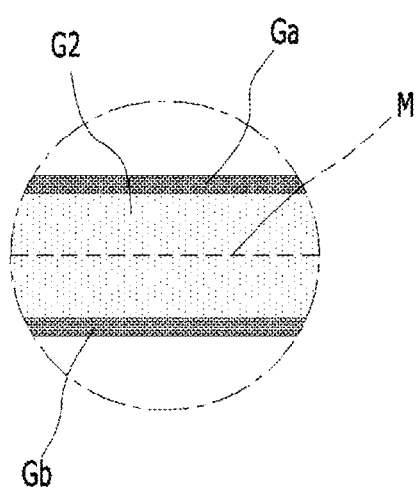
FIG. 6 is an enlarged cross-sectional view of a part "B" of FIG. 1.

The completely dried gel sheet G2 forms a thin sheet shape such that a mesh pattern of the supporting member M contained therein is exposed to the outside, as illustrated in the photo of the actual object of FIG. 5. However, the front and rear surfaces are ironed so that as illustrated in FIG. 6, the surfaces are formed to be films Ga and Gb and the density those of is higher than the center portion close to the supporting member M.

In the above-described manufacturing apparatus of the exemplary embodiment of the present invention, the arrangement of the heater roll group 64 is not limited to the exemplary embodiment but may be modified if necessary.

Figure 7:
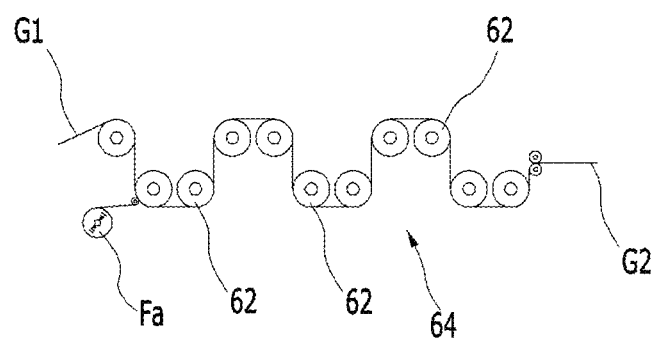
FIG. 7 is a side view illustrating another arrangement example of a heating roller group of FIG. 1.

FIG. 7 is a diagram illustrating another arrangement example of the heater roll group 64. Two heater rolls 62 which are disposed in parallel to form a pair are divided into two rows in a vertical direction. According to this structure, the front and rear surfaces of the sheet shaped solidified gel G1 may also be in sufficient contact with the heater roll 62 so that the completely dried gel sheet G2 may be manufactured at a high speed.

Figure 8:
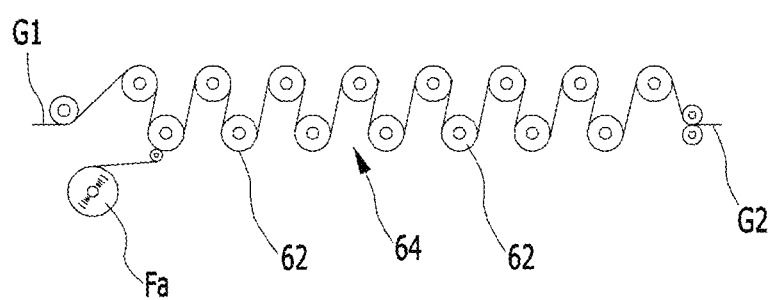
FIG. 8 is a side view illustrating still another arrangement example of a heating roller group of FIG. 1.

Further, as illustrated in FIG. 8, even though the sheet shaped solidified gel G1 is disposed so as to be driven while rounding half a circumstance of the heater roll 62, similarly, the gel sheet G2 may be manufactured at a high speed.

Figure 9:
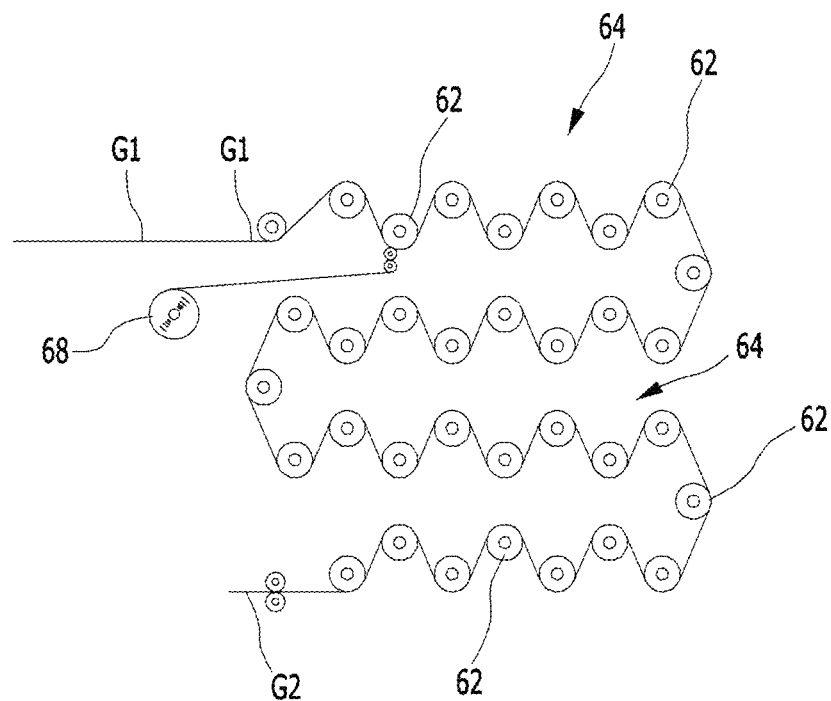
FIG. 9 is a side view illustrating another arrangement example of a heating roller group of FIG. 1.

FIG. 9 is a diagram illustrating another arrangement example of the heater roll group 64. Two heater rolls 62 which are disposed in a vertical direction to form a pair are disposed to have a reduced interval so that a distance where the sheet shaped solidified gel G1 turns around the heater roll 62 is increased. Therefore, a completely dried gel sheet G2 may be obtained.

Figure 10:
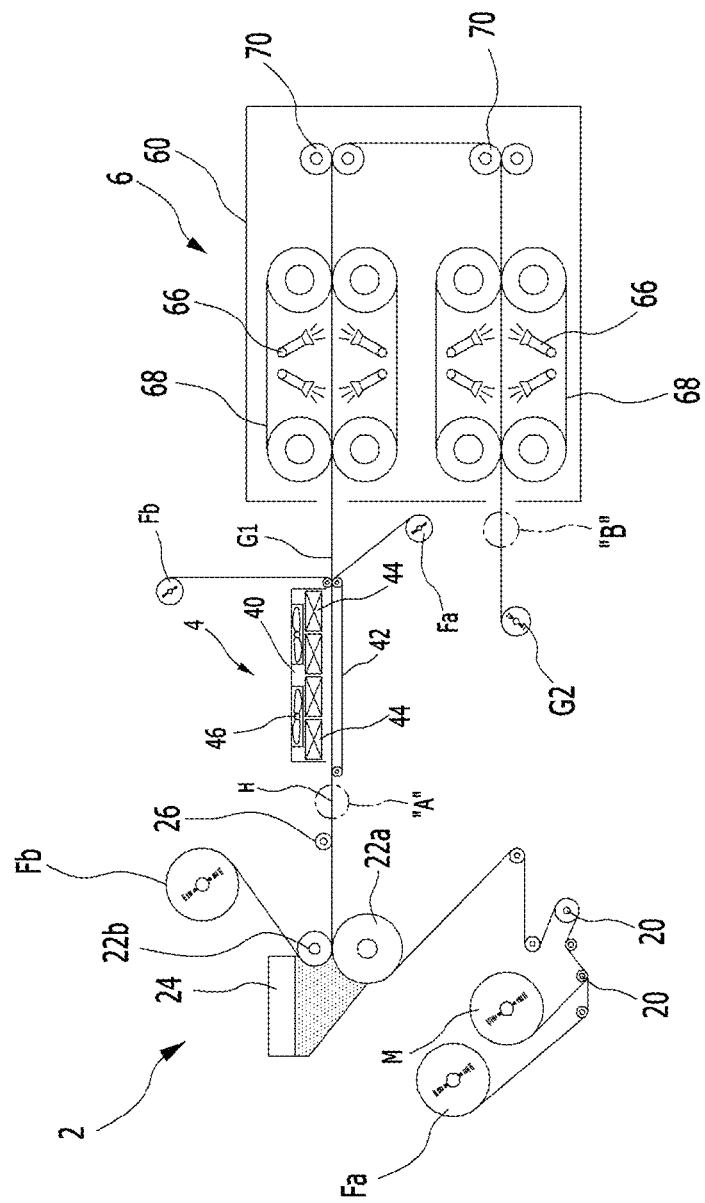
FIG. 10 is a schematic side view illustrating another configuration example of a major heating drying unit of a gel sheet manufacturing apparatus according to an exemplary embodiment of the present invention.

FIG. 10 is another exemplary embodiment of a dried gel sheet manufacturing apparatus according to the present invention. The dried gel sheet manufacturing apparatus includes an applying unit 2, a cooling drying unit 4, and a heating drying unit 6. The applying unit 2 is configured by a plurality of guide rolls 20, gravure rolls 22a and 22b, and a reserving tank 24 in which a hydrogel composition is reserved. In the cooling drying unit 4, a conveyer 42 is disposed on a lower surface in the cooling housing 40 provided with an inlet and an outlet at both sides and equipment required for low temperature cooling such as a cooling plate 44 and a ventilator 46 is disposed thereon. The configuration of this exemplary embodiment is same as the above-described dried gel sheet manufacturing apparatus of FIG. 1.

However, in this exemplary embodiment, a nozzle unit 66 which supplies warm air is disposed in the heating housing 60 provided with the inlet and the outlet in the heating drying unit 6 and a pair of dry conveyors 68 is disposed around the nozzle unit 66 to be opposite to each other in a vertical direction. A plurality of pairs of dry conveyors may be provided. Further, a plurality of godet rollers 70 is disposed between adjacent dry conveyors 68 to accelerate the drying of the hydrogel composition, which is different from the configuration of the above-described exemplary embodiment.

In this exemplary embodiment, the warm air sprayed from the nozzle unit 64 is in the range of 180 to 200° C. and the godet roller 66 is desirably heated to 70 to 80° C.

In the dried gel sheet manufacturing apparatus with the above-described configuration, the sheet shaped solidified gel G1 which passes through the cooling drying unit 4 passes through one pair of dry conveyers 68 in the heating housing 60. During this process, the sheet shaped solidified gel moves while the front and rear surfaces are dried with the warm air of the nozzle unit 66 and continuously passes through the godet roller 66 so that the front and rear surfaces are ironed.

Figure 11:
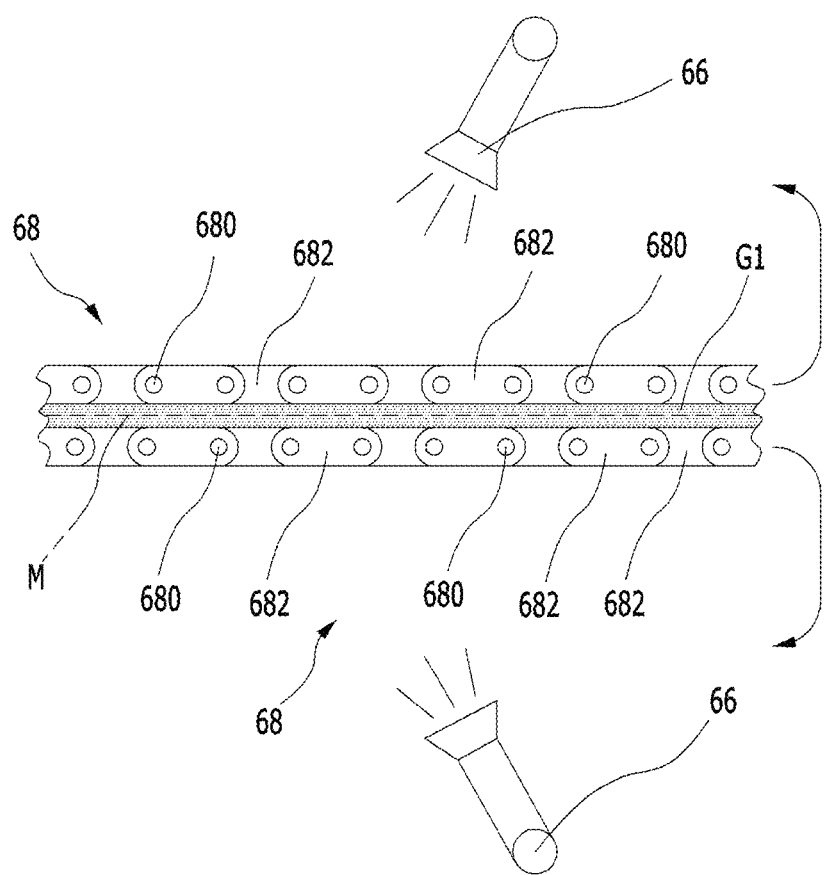
FIG. 11 is a schematic side view illustrating a detailed configuration of a dry conveyor applied to the dried gel sheet manufacturing apparatus of FIG. 10.

In the meantime, in this exemplary embodiment, as illustrated in FIG. 11, the dry conveyor 68 may adopt a link conveyer with a structure in which a plurality of link members 682 is disposed with an equal distance between connecting shafts 680 which are endlessly disposed. Further, even though not illustrated, like an example in which a belt in which innumerable holes are formed on a plate or a non-woven fabric, or a net is endlessly disposed between one pair of wheels, when an arbitrary structure exposes the front and rear surfaces of the sheet shaped solidified gel G1 with the warm air blown out from the nozzle unit 66, any structure may be adopted.

In the above-described manufacturing apparatus of the exemplary embodiment of the present invention, the godet roller 66 is not limited to be disposed as described in the above exemplary embodiment, but the position thereof may be modified or another unit may be added thereto if necessary.

Figure 12:
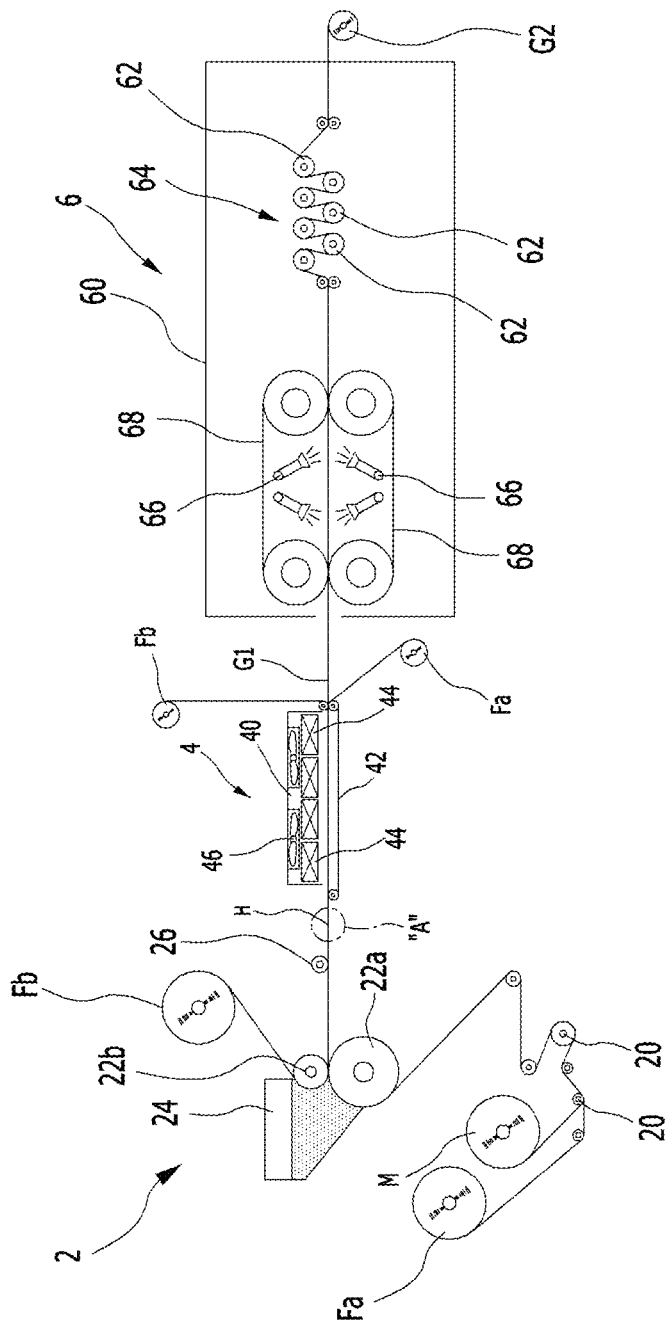
FIG. 12 is a schematic side view illustrating another configuration example of a heating drying unit of FIG. 10.

For example, as illustrated in FIG. 12, the heater roll group 70 which includes a plurality of heater rolls 68 is disposed continuously as the dry conveyer 62. In this case, the sheet shaped solidified gel G1 finally passes through the heater roll group 70 so that the front and rear surfaces are tightly ironed so that a more preferable property of the films Ga and Gb may be obtained.

The heater roll group 70 is configured to equally dispose the heater rolls 68 in two rows in a vertical direction to form a pair so that the sheet shaped solidified gel G1 which is driven between the heater rolls 68 is not damaged to be cut due to a tensile action.

Figure 13:
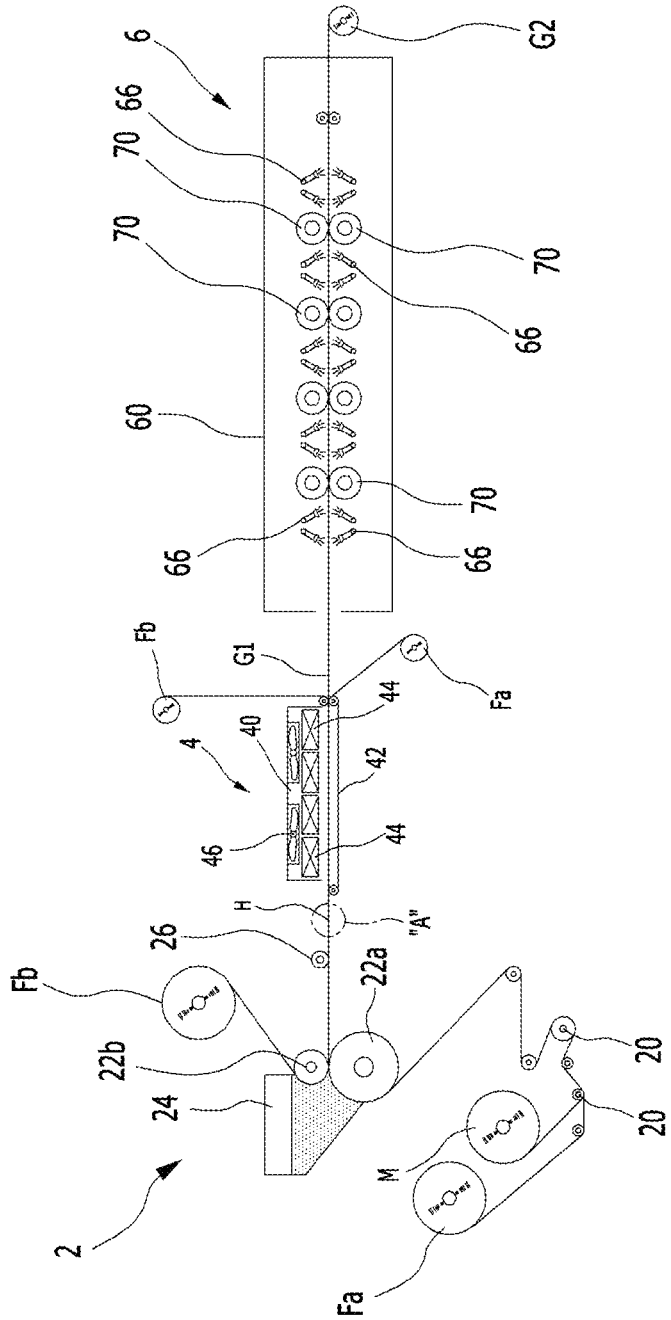
FIG. 13 is a schematic side view illustrating another configuration example of the heating drying unit of FIG. 10.

As another example of the above-described heating drying unit 6, as illustrated in FIG. 13, in the heating housing 60, a plurality of nozzle units 64 and a plurality of godet rollers 66 are alternately disposed so that the sheet shaped solidified gel G1 is repeatedly dried and ironed while moving and thus a desired dry gel G2 in which the front and rear surfaces are formed to be films Ga and Gb may be obtained.

Figure 14:
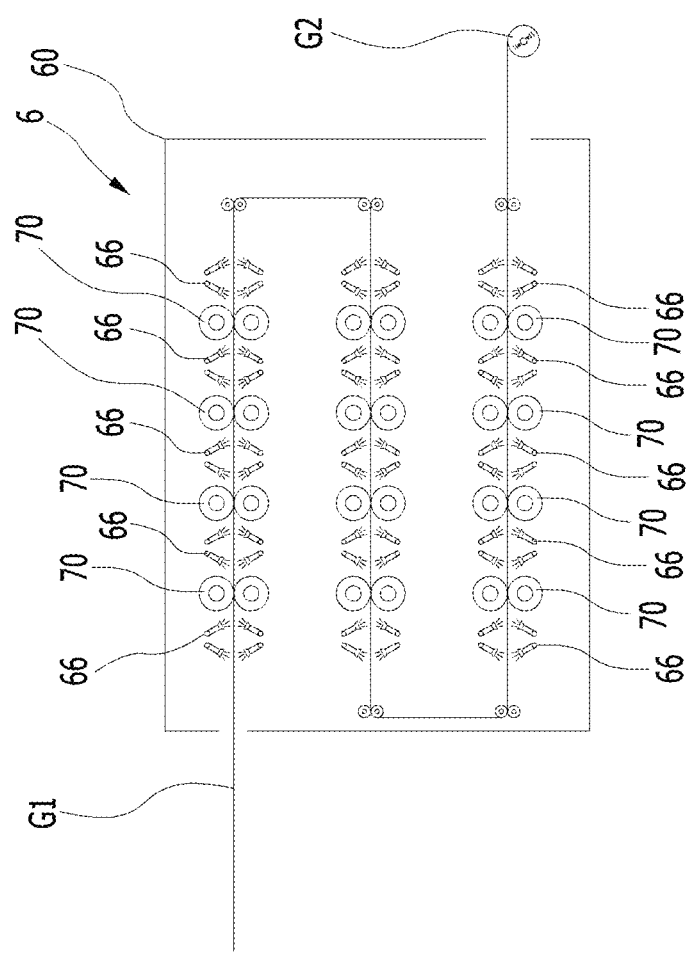
FIG. 14 is a schematic side view illustrating another configuration example of a heating drying unit of FIG. 10.

As illustrated in FIG. 14, a plurality of sets of the nozzle unit 64 and the godet roller 66 may be disposed. In this case, a gel sheet G2 in which the front and rear surfaces are more tightly formed to be films may be obtained.

A manufacturing method of the exemplary embodiment of the present invention using the dried gel sheet manufacturing apparatus with the above-described configuration is performed by an applying step of applying a hydrogel composition on a supporting member M supplied along a lower film Fa to have a sheet shape and covering an upper film Fb on a top surface thereof to protect a sheet shaped hydrogel, a cooling drying step of cooling the sheet shaped hydrogel at a low temperature atmosphere to be changed to a sheet shaped solidified gel G1, and a heating drying step of separating upper and lower films Fb and Fa from the sheet shaped solidified gel G1 obtained by the cooling and drying the sheet shaped solidified gel with hot air while passing through the dry conveyor 66 and the godet roller 70 so that front and rear surfaces are tightly dried by ironing to obtain a gel sheet G2.

Further, a gel sheet of the exemplary embodiment of the present invention obtained by the above-described dried gel sheet manufacturing method is formed to be films Ga and Gb because a density of the front and rear surfaces is higher than that of a center portion close to the supporting member M due to the ironing action applied on the gel sheet while passing through the heater roll 62 or between the dry conveyor 66 and godet roller 70.

Some parts of the films Ga and Gb are not recognizable from an actual dried gel sheet of FIG. 5 by naked eyes. The films may be formed to have a cross-section in which air gap distribution is reduced, which may result in reducing an amount of water particles which passes through the gel sheet per hour. Therefore, when the gel sheet G2 is used by dipping the gel sheet in a specific drug or a cosmetic composition to return to the original hydrogel state, the contained specific drug or cosmetic composition is suppressed from being vaporized by passing through the cross-section.

The fact that the gel sheet G2 according to the exemplary embodiment of the present invention has a vaporization suppressing effect through a surface will be confirmed through the following comparative test example 1.

Comparative Test Example 1

Hydrogel Vaporizing Test

Hydrogel which is obtained by dipping a specimen obtained by cutting a gel sheet G2 obtained during the manufacturing process according to an exemplary embodiment of the present invention by 4×4 cm in a 20 g distilled water and swelling the specimen for 15 minutes is prepared as a specimen.

Next, the hydrogel manufactured by the related art using a component same as the gel sheet G2 is cut with the same size to prepare a comparative specimen.

Weights of the specimen and the comparative specimen are measured under the same condition and the specimen and the comparative specimen are put in a moisture analyzer MAC 50/NH model manufactured by RADWAG WAGI Elektroniczne of Poland. Change of weight in accordance with elapse of time is converted into percentage while maintaining a temperature at 40° C. and the result thereof is represented in Table 1.

TABLE 1

| | Moisture vaporization rate (unit: %) | |
|---|---|---|
| Time | Specimen of the present invention | Comparative specimen of the related art |
| 5 min | 1.71 | 2.96 |
| 10 min | 3.47 | 6.15 |
| 20 min | 6.98 | 12.62 |
| 30 min | 10.45 | 18.69 |
| 45 min | 15.59 | 28.04 |
| 60 min | 20.77 | 37.07 |
| 75 min | 25.87 | 45.87 |
| 90 min | 31.05 | 54.51 |

As seen from Table 1, a change of the vaporization rate of the specimen of the present invention is increased 1.76→3.51→3.47→5.14→5.18→5.1→5.18 as time has elapsed. However, the change of the vaporization rate of the comparative specimen of the related art is 3.19→6.47→6.07→9.35→9.03→8.8→8.64, which is higher than that of the present invention. Therefore, the specimen of the present invention has an excellent moisturizing effect.

As described above, in the exemplary embodiment of the present invention, a vaporization rate in a state when the gel sheet G2 is converted back to a hydrogel to be used as a beauty pack is lower than the hydrogel with the same component as the related art. This is because a density of the ironed front and rear surfaces is higher than the density of the center portion so that an inner air gap thereof is reduced so that the amount of passing moisture is restricted and the vaporization is suppressed.

However, when the gel sheet G2 obtained by the above-described manufacturing method according to the exemplary embodiment of the present invention is stored for a long time, surfaces which are in contact with each other are undesirably bonded to cause a problem. Therefore, it is recommended to use the gel sheet G2 as soon as possible.

Figure 15:
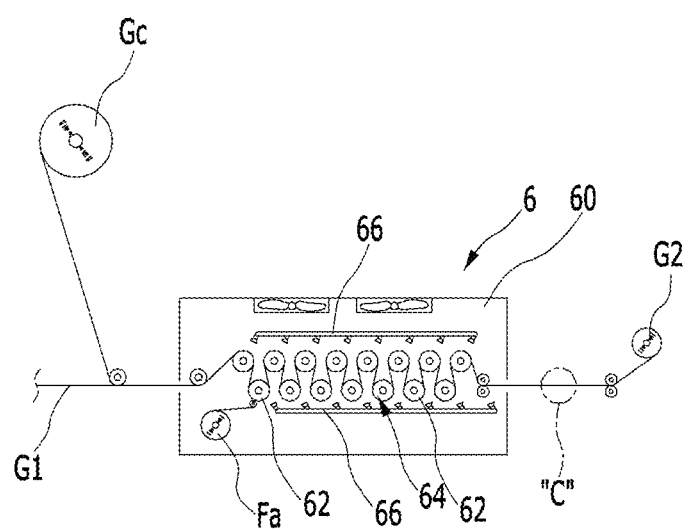
FIG. 15 is a side view of main parts of a dried gel sheet manufacturing apparatus according to another exemplary embodiment of the present invention.

However, the above-described problem may be solved by covering a top surface of the sheet shaped solidified gel G1 which is discharged from the cooling drying unit 4 to separate the upper film Fb therefrom, during the manufacturing process, with a release paper Gc again and then allowing the sheet shaped solidified gel G1 to pass through the heating drying unit 6, as illustrated in FIG. 15.

Figure 16:
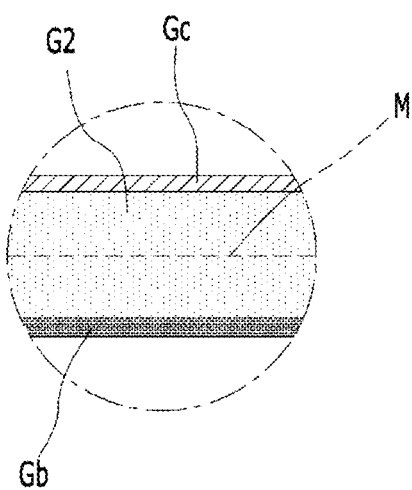
FIG. 16 is an enlarged cross-sectional view of a part "C" of FIG. 15.

The sheet shaped solidified gel G1 covered with the release paper Gc passes between the heater rolls 62 to be dried to be a gel sheet G2. However, as illustrated in FIG. 16, the film formation of the top surface on which the release paper Gc is covered is not significantly progressed but only a lower surface on which the lower film Fa is separated is formed to be film Gb. Therefore, it is required to provide a visual mark to distinguish the front and rear surfaces.

That is, the gel sheet obtained from the exemplary embodiment of the present invention may be manufactured as a skin protecting patch which replaces a bandage for injury treatment or a large size gauze or a patch for improvement of wrinkles around eyes or lips or neck wrinkles or a cosmetic facial pack, and in this case, when a mark to recommend a user to use a surface which is not formed as a film to be in contact with a skin is added, the usage effect may be doubled.

Figure 17:
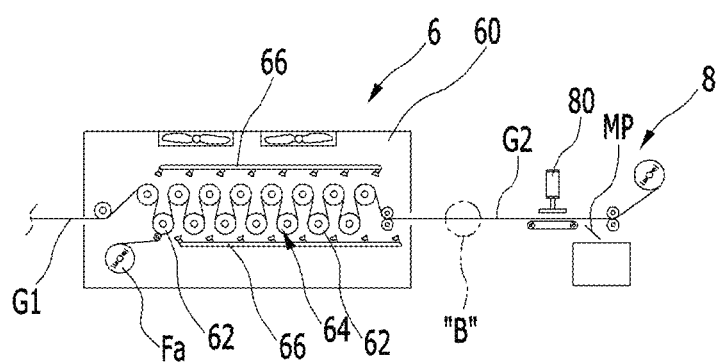
FIG. 17 is a schematic diagram illustrating a process of manufacturing a dried gel sheet of the present invention to be a beauty pack.

FIG. 17 illustrates an exemplary embodiment in which the above-described gel sheet G2 is manufactured to be a beauty pack MP.

In this exemplary embodiment, the gel sheet G2 which passes through the heating drying unit 6 to be completely dried is continuously transported to a forming unit 8 and then passes through a press machine 80. Therefore, a gel sheet which is pressed to be a mask body MP having a predetermined shape and the remaining part after being pressed is separately restored.

A fact that the gel sheet G2 which is adopted as a material of the beauty pack of the exemplary embodiment of the present invention suppresses the vaporization through the surface is proved by Comparative test example 1.

Further, characteristics of the gel sheet G2 which is manufactured as a beauty pack G2 is represented by the following Comparative test examples 2 to 4.

Comparative Test Example 2

Hydrogel Adhering Test

A specimen of the exemplary embodiment of the present invention used in Comparative test example 1 and a comparative test are adhered on a cheek of a human body and an area where the specimen and the cheek are in contact with each other is calculated at every 10 minutes, to compare the adhesiveness.

Figure 20:
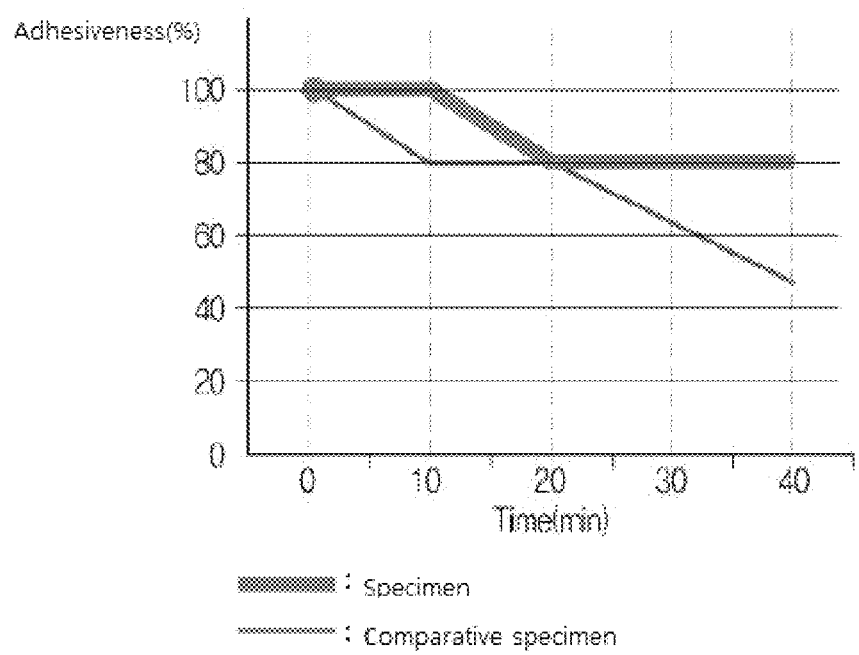
FIG. 20 is a graph illustrating a comparison result between time and adhesiveness.

A comparison result is illustrated in FIG. 20.

An adhered state of the specimen of the exemplary embodiment of the present invention is maintained until 10 minutes has elapsed after being adhered on a face and the adhesiveness is deteriorated to be 80% after 10 minutes and then maintained until 40 minutes has elapsed. In contrast, the adhesiveness of the hydrogel of the related art is reduced after being adhered on the face and is deteriorated to be 80% after 10 minutes and this state is maintained until 20 minutes has elapsed. Thereafter, the adhesiveness is reduced in proportion to the elapsed time.

According to the above results, it is understood that the adhesiveness of the specimen of the exemplary embodiment of the present invention is significantly improved as compared with the adhesiveness of the hydrogel of the related art.

Comparative Test Example 3

Contraction Test of Hydrogel

A hydrogel which is obtained by dipping a specimen obtained by cutting the gel sheet G2 of the exemplary embodiment of the present invention by 3.5×3.5 cm in a 20 g distilled water and swelling the specimen for 15 minutes is prepared as a specimen.

Next, the hydrogel manufactured by the related art using a component same as the gel sheet G2 is cut with the same size to prepare a comparative specimen.

A specimen to be compared and a comparative specimen are left at a room temperature atmosphere for 120 minutes and a length of each side is measured at every 30 minutes to compare a contraction rate. The comparison result is represented in the following Table 2.

TABLE 2

| Time | Specimen of the present invention | Comparative specimen of the related art |
|---|---|---|
| 0 min | 3.5 | 3.5 |
| 30 min | 3.4 | 3.4 |
| 60 min | 3.2 | 3.4 |
| 90 min | 3.1 | 3.3 |
| 120 min | 3.0 | 3.2 |

In the result of Table 2, the results of the specimen of the exemplary embodiment of the present invention and the comparative specimen of the related art are same until 30 minutes elapses. Thereafter, the specimen of the exemplary embodiment of the present invention more contracts.

When the hydrogel is adhered on the skin, the hydrogel contracts as time has elapsed to lift the skin so that the contraction phenomenon acts as a lifting effect.

The reason why the specimen of the exemplary embodiment of the present invention contracts more than the comparative specimen of the related art is that the specimen of the exemplary embodiment of the present invention is obtained by converting the dried gel sheet back to the hydrogel. Therefore, as compared with the comparative sheet of the related art which is originally formed to be a hydrogel, the specimen of the exemplary embodiment of the present invention more contracts even by slight moisture vaporization.

Comparative Test Example 4

Skin Moisturizing Test

The specimen prepared in Comparative test example 1 and a comparative specimen are added to one natural leather and left for 30 minutes and then a moisturizing rate of the leather surface for every added position is measured. The result is represented in the following Table 3.

A measurement value of Table 3 is a moisturizing rate of a surface of the natural leather which is adopted instead of the skin. The value is measured when the specimen is added and 30 minutes has elapsed after adjusting a value measured before adding the specimen to be 100. In this case, as a measuring device, Cutometer MAP 580 manufactured by Courage-khazaka of Germany is used.

TABLE 3

| | Moisturizing rate (%) | |
|---|---|---|
| Classification | Specimen of the present invention | Comparative specimen of the related art |
| Before adding | 100 | 100 |
| After adding | 140 | 128 |

As seen from the result in Table 3, it is understood that the moisturizing rate of the hydrogel which is manufactured using a gel sheet of the exemplary embodiment of the present invention as a material is 1.12 times better than the hydrogel of the related art.

Figure 18:
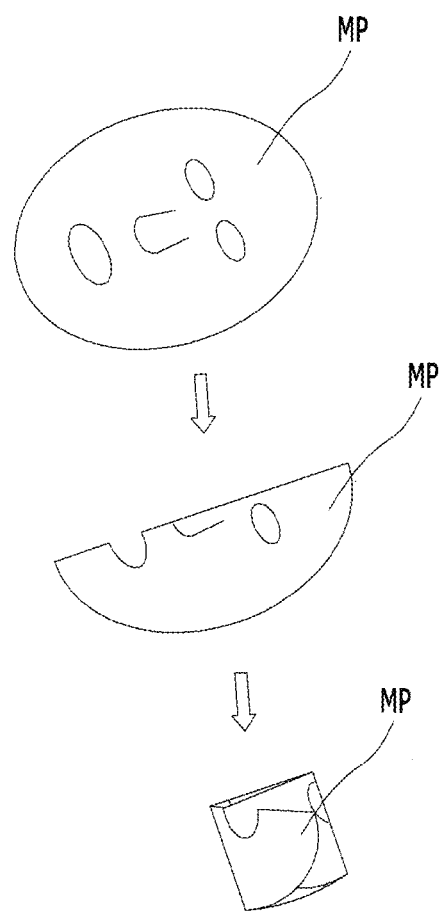
FIG. 18 is a view explaining a packing process of a beauty pack which is formed of a dried gel sheet of the present invention.

As described above, the mask body MP of the exemplary embodiment of the present invention collected when the gel sheet G2 passes through the press machine 80 of the forming unit 8 has an excellent characteristic. Further, as illustrated in FIG. 18, the mask body MP is folded in half and then folded twice in a length direction by one third. The reduced mask body is packed in a normal pouch with a cosmetic essence to be manufactured as a final product.

However, the mask body MP of the present invention is not limited to the above-described exemplary embodiment, but like the gel sheet G2 obtained from the apparatus illustrated in FIG. 16, the mask body to which a wet strength paper Gc is added may be manufactured.

In this case, when a user adheres the mask on the skin without stripping off the wet strength paper Gc, the wet strength paper Gc restricts the moisture from being vaporized so that moisturizing effect of the skin is more improved.

In contrast, when a surface from which the wet strength paper Gc is stripped is in contact with the skin, the surface which is not formed as a film is in contact with the skin so that the user may feel the same touch as the hydrogel mask pack of the related art.

Moreover, in the device of FIG. 16, when powder or extract of an essential cosmetic component such as hyaluronic acid, tocopherol, or retinol is applied on the sheet shaped solidified gel G1 immediately before covering the sheet shaped solidified gel with the wet strength paper Gc and then the sheet shaped solidified gel is protected by being covered with the wet strength paper Gc, the essential cosmetic component is concentrated on the skin while applying the pack on the user. Therefore, significantly improved beauty effect may be achieved.

Further, instead of the cosmetic component, a chemical therapy component for injury treatment may be applied.

In the exemplary embodiment of the present invention, as the wet strength paper Gc, a wet strength paper containing epoxy based polyaminoamide epichlorohydrin resin is adopted. The above-mentioned wet strength paper is a sort of permanent wet strength agents. Even though the wet strength paper is in continuously contact with the moisture, the strength is less deteriorated. Therefore, the wet strength paper is suitable for the present invention.

Figure 19:
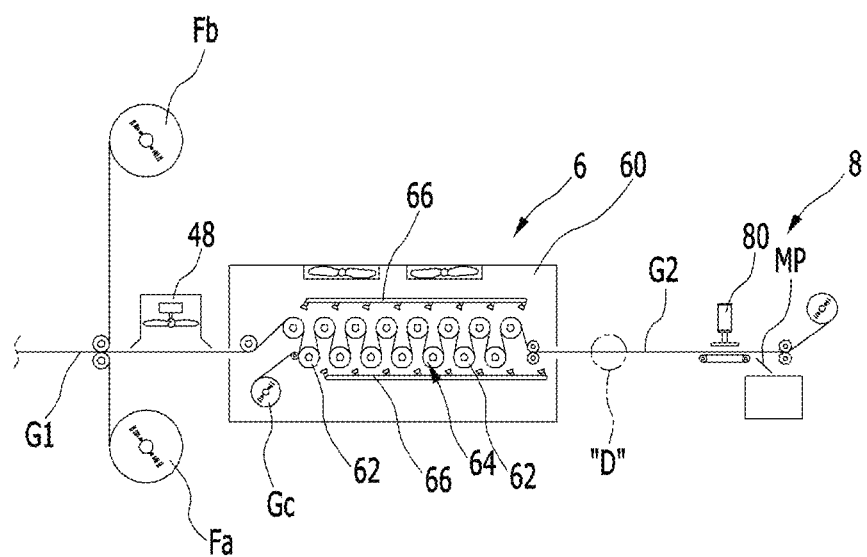
FIG. 19 is a schematic diagram illustrating another exemplary embodiment of a manufacturing apparatus of a beauty pack which is formed of a dried gel sheet of the present invention.

Further, the wet strength paper Gc may cover the mask body in the entrance of the heating drying unit 6, as illustrated in FIG. 19. Further, a pre drier 48 is disposed in the middle of the path which passes through the cooling drying unit 4 and is transported to the heating drying unit 6 so that the surface of the sheet shaped solidified gel G1 from which the upper film Fa is separated is dried in advance to help the drying in the heating drying unit 6.

To the contrary of the cross-section of the gel sheet illustrated in FIG. 17, a surface of the gel sheet G2 obtained by the manufacturing apparatus of FIG. 19 is formed to be a film and a wet strength paper 68 is covered on a rear surface. However, both are fundamentally equal.

<Description of symbols>

| | |
|---|---|
| 2: Applying unit | |
| 20: Guide roll | 22a, 22b: Gravure roll |
| 24: Reserving tank | 26: Guider |
| 4: Cooling drying unit | |
| 40: Cooling housing | 42: Conveyor |
| 44: Cooling plate | 46: Ventilator |
| 6: Heating drying unit | |
| 60: Heating housing | 62: Heater roll |
| 64: Heater roll group | 66: Nozzle unit |
| 68: Dry conveyor | 70: Godet roller |
| 8: Forming unit | 80: Press machine |
| Fa, Fb: Lower and upper film | G1: Sheet shaped solidified gel |
| G2: Gel sheet | Gc: Releasing paper |
| Ga, Gb: Film formation | H: Sheet shaped hydrogel |
| M: Supporting member | |

What is claimed is:

1. A dried gel sheet manufacturing method by a dried gel sheet manufacturing apparatus comprising:

an applying unit which includes gravure rolls to apply a hydrogel composition reserved in a reserving tank on a supporting member M which is conveyed together with a lower film Fa, an upper film Fb being adhered onto a top surface of a sheet shaped hydrogel H applied on the supporting member M while moving the sheet shaped hydrogel H;

a cooling drying unit in which a conveyer which transports the sheet shaped hydrogel H protected by the upper and lower films Fb and Fa is disposed on a bottom of a cooling housing and a cooling plate which cools the sheet shaped hydrogel H to be converted into a sheet shaped solidified gel G1 is disposed above the conveyer; and a heating drying unit which includes a heater roll group formed by a plurality of heater rolls and a nozzle unit which supplies warm air between heater rolls in the heating housing and passes the sheet shaped solidified gel G1 from which the upper and lower films Fb and Fa are separated through the heater roll group so that front and rear surfaces thereof are heated and dried by the ironing and warm air to be converted into a gel sheet G2, and the method comprising:

an applying step of applying a hydrogel composition on a lower film Fa to form a sheet shaped hydrogel H including a supporting member M and adhering an upper film Fb on a top surface to protect the sheet shaped hydrogel;

a cooling drying step of passing through the sheet shaped hydrogel H at a low temperature atmosphere to be converted into a sheet shaped solidified gel G1; and a heating drying step of ironing front and rear surfaces of the sheet shaped solidified gel G1 from which the upper and lower films Fb and Fa are separated and heating and drying the front and rear surfaces with warm air to obtain a gel sheet G2.

2. The method of claim 1, wherein:
in the heating drying step, the sheet shaped solidified gel G1 is ironed and heated and dried with a warm air after covering a top surface of the sheet shaped solidified gel G1 with a releasing paper Gc.

* * * * *